US00PP18353P2

(12) United States Plant Patent
Hoogenraad

(10) Patent No.: US PP18,353 P2
(45) Date of Patent: Dec. 25, 2007

(54) ***EUONYMUS* PLANT NAMED 'HOOIJ'**

(50) Latin Name: *Euonymus fortunei*
Varietal Denomination: Hooij

(75) Inventor: Gerrit Hoogenraad, WB Ederveen (NL)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 11/494,159

(22) Filed: Jul. 27, 2006

(51) Int. Cl.
*A01H 5/00* (2006.01)

(52) U.S. Cl. ..... Plt./246

(58) Field of Classification Search ..... Plt./246
See application file for complete search history.

*Primary Examiner*—Kent Bell
(74) *Attorney, Agent, or Firm*—C. A. Whealy

(57) ABSTRACT

A new and distinct cultivar of *Euonymus* plant named 'Hooij', characterized by its compact outwardly spreading plant habit; yellow and dark green variegated leaves with random speckles; and leaves twisting in aspect.

1 Drawing Sheet

Botanical designation: *Euonymus fortunei.*
Cultivar denomination: 'HOOIJ'.

BACKGROUND OF THE INVENTION

The present invention relates to a new and distinct cultivar of *Euonymus,* grown as an ornamental shrub, botanically known as *Euonymus fortunei* and hereinafter referred to by the name 'Hooij'.

The new *Euonymus* is a naturally-occurring branch mutation of the *Euonymus fortunei* cultivar Sunspot, disclosed in U.S. Plant Pat. No. 4,340. The new *Euonymus* was discovered and selection by the Inventor from within a population of plants of the cultivar Sunspot in a controlled environment in Ederveen, The Netherlands in March, 2001.

Asexual reproduction of the new *Euonymus* by cuttings in a controlled environment in Ederveen. The Netherlands since June, 2001, has shown that the unique features of this new *Euonymus* are stable and reproduced true to type in successive generations.

SUMMARY OF THE INVENTION

The cultivar Hooij has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Hooij'. These characteristics in combination distinguish 'Hooij' as a new and distinct cultivar of *Euonymus:*

1. Compact outwardly spreading plant habit.
2. Yellow and dark green variegated leaves with random speckles.
3. Leaves twisting in aspect.

Plants of the new *Euonymus* differ from plants of the parent, the cultivar Sunspot, in the following characteristics:

1. Leaves of plants of the new *Euonymus* are more twisting than leaves of plants of the cultivar Sunspot.

2. Plants of the new *Euonymus* and the cultivar Sunspot differ in leaf coloration as plants of the cultivar Sunspot are not speckled.

Plants of the new *Euonymus* can also be compared to plants of the cultivar Harlequin, not patented. Plants of the new *Euonymus* differ from plants of the cultivar Harlequin in the following characteristics:

1. Plants of the new *Euonymus* are more tolerant to high light and low temperatures than plants of the cultivar Harlequin.
2. Plants of the new *Euonymus* and the cultivar Harlequin differ in leaf coloration as plants of the cultivar Harlequin have speckled white and green variegated leaves.

BRIEF DESCRIPTION OF THE PHOTOGRAPHS

The accompanying colored photographs illustrate the overall appearance of the new *Euonymus,* showing the colors as true as it is reasonably possible to obtain in colored reproductions of this type. Colors in the photographs may differ slightly from the color values cited in the detailed botanical description which accurately describe the colors of the new *Euonymus.*

The photograph at the top of the sheet comprises a side perspective view of a typical plant of 'Hooij' grown in an outdoor nursery.

The photograph at the bottom of the sheet is a close-up view of a typical plant of 'Hooij' grown in an outdoor nursery.

DETAILED BOTANICAL DESCRIPTION

The aforementioned photographs and following observations, measurements and values describe plants grown in Ederveen, The Netherlands, under commercial practice in containers in an outdoor nursery. Plants had been growing for about two years when the photographs and description were taken. In the following description, color references are made to The Royal Horticultural Society Colour Chart, 1995 Edition, except where general terms of ordinary dictionary significance are used.

Botanical classification: *Euonymus fortunei* cultivar Hooij.

Parentage: Naturally-occurring branch mutation of the *Euonymus fortunei* cultivar Sunspot, disclosed in U.S. Plant Pat. No. 4,340.

Propagation:

*Type.*—By cuttings.

*Time to initiate roots, summer.*—About 20 days at 23° C.

*Time to initiate roots, winter.*—About 35 days at 15° C.

*Time to produce a rooted young plant, summer.*—About three months at 20° C.

*Time to produce a rooted young plant, winter.*—About six months at 15° C.

*Root description.*—Fine; white in color.

*Rooting habit.*—Freely branching; dense.

Plant description:

*Plant form/habit.*—Compact, outwardly spreading subshrub; dense and bushy appearance. Moderately vigorous growth habit.

*Plant height.*—About 19 cm.

*Plant width* (*spread*).—About 33 cm.

*Lateral branches.*—Length: About 33 cm. Diameter: About 3 cm. Internode length: About 4 mm to 2.4 cm. Strength: Strong. Texture: Smooth, glabrous. Color: Close to 7B to 144A.

Foliage description:

*Arrangement.*—Opposite, simple.

*Length.*—About 2.7 cm.

*Width.*—About 1.5 cm.

*Shape.*—Ovate.

*Apex.*—Acute.

*Base.*—Attenuate.

*Margin.*—Entire.

*Aspect.*—Twisting.

*Texture, upper and lower surfaces.*—Smooth, glabrous.

*Venation pattern.*—Pinnate.

*Color.*—Developing leaves, upper surface: Yellow, 7B, and dark green, 133A; speckled with 191C. Developing leaves, lower surface: 148D. Fully developed leaves, upper surface: Yellow, 7D, and dark green, 131A; speckled with 191C; venation, similar to lamina. Fully developed leaves, lower surface: 148B; venation, 148B.

*Petiole.*—Length: About 3 mm. Diameter: About 1 mm. Texture, upper and lower surfaces: Smooth, glabrous. Color, upper and lower surfaces: 154C.

Flower description: Flower initiation and development has not been observed on plants of the new *Euonymus*.

Disease/pest resistance: Plants of the new *Euonymus* have not been noted to be resistant to pathogens and pests common to *Euonymus*.

Temperature tolerance: Plants of the new *Euonymus* have been observed to tolerate temperatures from about −17° C. to about 35° C.

It is claimed:

1. A new and distinct *Euonymus* plant named 'Hooij' as illustrated and described.

* * * * *

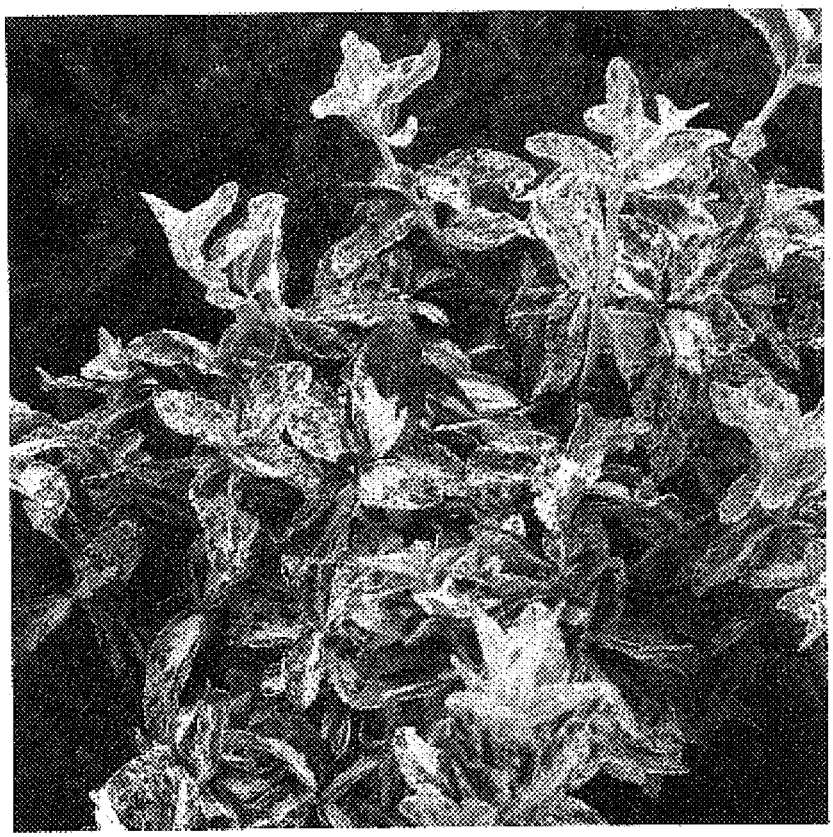
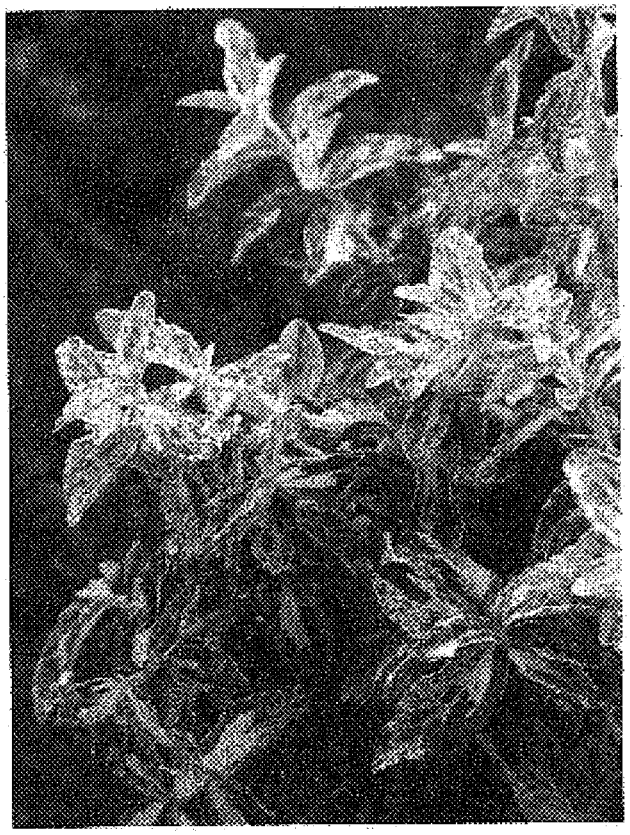

UNITED STATES PATENT AND TRADEMARK OFFICE

CERTIFICATE OF CORRECTION

PATENT NO. : PP18,353 P2
APPLICATION NO. : 11/494159
DATED : July 24, 2012
INVENTOR(S) : Gerrit Hoogenraad It is certified that error appears in the above-identified patent and that said Letters Patent is hereby corrected as shown below:

Title Page, Item (54) and in the Specification at Column 1, line 1, Title "HOOIJ" should correctly read --HOOGI--.

Title Page, Item (50) "Varietal Denomination: Hooij" should correctly read --Varietal Denomination: Hoogi--

Title Page, Item (57) Abstract, line 2, "Hooij" should correctly read --Hoogi--

Column 1, lines 8, 25, 31, and 32; Column 2, lines 26 and 29; Column 3, line 1;
Column 4, line 27 (Claim 1, line 1), varietal denomination "Hooij" should correctly read --Hoogi--.

Signed and Sealed this
Twenty-third Day of July, 2013

Teresa Stanek Rea
*Acting Director of the United States Patent and Trademark Office*